United States Patent [19]
Dumas et al.

[11] Patent Number: 5,811,585
[45] Date of Patent: Sep. 22, 1998

[54] PROCESS FOR PREPARING 5-CHLORO-2,3-DIHYDRO-1H-INDEN-1-ONE

[75] Inventors: Donald Joseph Dumas; Sourav Kumar Sengupta, both of Wilmington, Del.; David Richard Corbin, West Chester, Pa.

[73] Assignee: E. I. du Pont de Nemours and Company, Wilmington, Del.

[21] Appl. No.: 860,344

[22] PCT Filed: Oct. 12, 1995

[86] PCT No.: PCT/US95/12726

§ 371 Date: Jun. 24, 1997

§ 102(e) Date: Jun. 24, 1997

[87] PCT Pub. No.: WO96/20151

PCT Pub. Date: Jul. 4, 1996

Related U.S. Application Data

[63] Continuation of Ser. No. 336,950, Dec. 28, 1994.

[51] Int. Cl.$^6$ .................................................. C07C 45/61

[52] U.S. Cl. ............................................. 568/316; 568/327
[58] Field of Search ...................................... 568/316, 327

[56] References Cited

U.S. PATENT DOCUMENTS

| | | | |
|---|---|---|---|
| 2,815,382 | 12/1957 | Carpenter et al. | 568/327 |
| 3,509,215 | 4/1970 | Wood et al. | 568/327 |
| 4,568,782 | 2/1986 | Pagnotte et al. | 568/327 |

OTHER PUBLICATIONS

Olivier et al, Bull de la Chim de France, vol. 11, pp. 3096–3099, 1973.

Marechal et al, Bull de la Chim de France, vol. 6 pp. 1981–1989, 1969.

*Primary Examiner*—James H. Reamer

[57] ABSTRACT

A process for preparing 5-chloro-2,3-dihydro-1H-inden-1-one comprising contacting 3-chloro-1-(chlorphenyl)-1-propanone with a catalyst selected from sulfuric acid and solid acid catalysts.

10 Claims, No Drawings

PROCESS FOR PREPARING 5-CHLORO-2,3-DIHYDRO-1H-INDEN-1-ONE

This application is a 371 of PCT/US95/12726, filed Oct. 12, 1995, which is a continuation of Ser. No. 08/336,950, filed Dec. 28, 1994.

BACKGROUND OF THE INVENTION

The present process provides an improved method for making 5-chloro-2,3-dihydro-1H-inden-1-one. Said inden-1-one is useful as an intermediate for making arthropodicidal oxadiazines such as methyl 7-chloro-2,5-dihydro-2-[[(methoxycarbonyl)[4-(trifluoromethoxy)-phenyl]amino] carbonyl]indeno[1,2-e][1,3,4]oxadiazine-4a(3H)-carboxylate which is disclosed in WO 92/11249.

A process for preparing 5-chloro-2,3-dihydro-1H-inden-1-one is disclosed in Olivier, M.; Marechal, E. *Bulletin de la Societe Chimique de France* (1973), 11, 3096–3099 where 3-chloro-1-(4-chlorophenyl)-1-propanone (alternately referred to as 3,4'-dichloropropiophenone) is treated with a mixture of aluminum chloride and sodium chloride at 180° C. Although the process disclosed in this reference begins with the same precursor as is used in the present process, the large amounts of aluminum chloride and sodium chloride required are difficult to handle, especially on a commercial scale at the required elevated temperature. In addition, any unused aluminum chloride and sodium chloride reactants and any by-products of the desired reaction represent a substantial disposal problem.

SUMMARY OF THE INVENTION

The present invention relates to an improved process for making 5-chloro-2,3-dihydro-1H-inden-1-one comprising adding a solution of 3-chloro-1-(4-chlorophenyl)-1-propanone in an inert solvent to sulfuric acid at 90°–150° C. in a way that minimizes byproduct reactions and product decomposition and maximizes yield and product purity.

In another embodiment, the present invention relates to an improved process for making 5-chloro-2,3-dihydro-1H-inden-1-one comprising contacting 3-chloro-1-(4-chlorophenyl)-1-propanone, optionally in the presence of an inert solvent, with a solid acid catalyst at 200°–425° C. in a continuous flow reactor. The process of the present invention is depicted by the following equation.

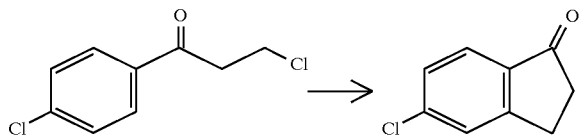

DETAILED DESCRIPTION OF THE INVENTION

In the present process, 3-chloro-1-(4-chlorophenyl)-1-propanone (hereafter, reactant) is contacted with sulfuric acid at a temperature of between about 90°–150° C. or with a solid acid catalyst at 200°–425° C. It is believed that under these conditions the reactant will rapidly eliminate HCl to form an intermediate, probably 1-(4-chlorophenyl)-2-propen-1-one. It is further believed that this intermediate then has the potential to react along at least two competing pathways: one path involves intramolecular cyclization to form the desired 5-chloro-2,3-dihydro-1H-1-one (hereafter, product), a second path involves intermolecular reaction between molecules of intermediate to form undesired oligomeric byproducts. Oligomeric byproducts are believed to represent the primary yield loss. Under the conditions defined above, the rate of dehydrochlorination of the reactant is believed to be fast relative to the rate at which the intermediate reacts to form product or byproduct.

In the embodiment of the present invention in which sulfuric acid is used, it has been found that product yield was increased by limiting the rate of addition of reactant to the reaction mixture and by diluting the reactant in inert solvent. It is believed that decreasing the rate of addition of the reactant to the reaction mixture and providing the reactant to the reaction mixture in dilute solution lowers the concentration of the intermediate in the reaction mixture. The rate of intramolecular cyclization of intermediate (to desired product) should be unaffected by concentration of the intermediate, whereas the rate of intermolecular reaction of the intermediate (to undesired oligomeric byproduct) should decrease with decreasing concentration of the intermediate.

In the embodiment of the present invention in which sulfuric acid is used, the rate of addition of reactant to the reaction mixture is in the range of about 0.05–1.0 moles of 3-chloro-1-(4-chlorophenyl)-1-propanone per liter of sulfuric acid (based on concentrated sulfuric acid, 95% by weight assay) per hour. At faster addition rates product yield becomes unacceptably low as formation of oligomeric byproduct becomes greater. At slower addition rates, the process becomes impractically slow for commercial operation, although the yield of product remains high. Preferably the rate of addition of reactant is about 0.05–0.5 moles of reactant per liter of sulfuric acid per hour, more preferably 0.1–0.3 moles of reactant per liter of sulfuric acid per hour.

In the embodiment of the present invention in which sulfuric acid is used, the reactant 3-chloro-1-(4-chlorophenyl)-1-propanone is in solution in an inert solvent when contacted with the sulfuric acid. The concentration of reactant in the solvent is not limited except by its solubility in the particular solvent selected. Dilution of reactant in solvent, at any concentration, provides better yield than contacting solid reactant directly with the sulfuric acid. High dilutions are preferred for maximum yield; dilution is only limited by practical considerations such as the difficulties of handling large reaction volumes and the cost of overly large reaction equipment. The concentration is preferably 0.1 to 1.0 molar, more preferably 0.2–0.5 molar.

The solvent used in conjunction with sulfuric acid can be any solvent which is inert to the reactants and to the reaction conditions including, for example, alkanes such as pentane, heptane, octane, petroleum ether, and chloroalkanes such as dichloromethane. Linear alkanes are preferred.

When the solution of 3-(chloro-1-(4-chlorophenyl)-1-propanone is added to the sulfuric acid, the reaction temperature is between about 90°–150° C. It has been found that at lower temperatures product yield becomes unacceptably low as formation of oligomeric and other byproducts becomes greater. At temperatures above about 150° C. in the presence of sulfuric acid, the desired product becomes unstable and tends to decompose. Preferably the present process is run at a reaction temperature of about 100°–125° C.

The sulfuric acid used in the present process is preferably concentrated sulfuric acid with an assay of at least about 95% by weight.

The reaction vessel and equipment can be any suitable vessel and equipment normally used in chemical processing.

As a safety precaution, because the solvents are combustible and the reaction temperature is relatively high, the process is preferably run under an inert atmosphere, preferably nitrogen. Hydrochloric acid gas is evolved as part of the process and the equipment should have scrubbers to prevent escape of the HCl to the environment.

The total amount of reactant 3-chloro-1-(4-chlorophenyl)-1-propanone added to the sulfuric acid is preferably about 20–406 grams (0.1–2.0 moles) per liter of sulfuric acid, more preferably about 51–203 grams (0.25–1.0 moles) per liter of sulfuric acid. The product will generally partition into the sulfuric acid phase, and can be recovered by any standard means such as quenching of the sulfuric acid phase over ice and collecting the separated solids by filtration.

In one embodiment of the present invention, the reactant is dissolved in a high-boiling solvent (boiling point above the reaction temperature) and the reactant solution added continuously or in small increments to the reaction vessel containing sulfuric acid maintained at the reaction temperature. Product forms and partitions into the sulfuric acid phase while the high-boiling solvent forms a separate phase on top of the sulfuric acid. The mixture is stirred gently during the course of the addition. The solution of reactant can optionally be preheated to reaction temperature prior to addition to the reaction vessel. Optionally, prior to the start of the addition, the sulfuric acid can be topped by a layer of high-boiling solvent. If the reaction vessel contains a lower sulfuric acid layer and an upper layer of high-boiling solvent, another option is to slowly add solid reactant to the upper solvent phase under conditions such that the reactant dissolves in the high-boiling solvent before there is any significant contact between the reactant and the sulfuric acid. The rate of addition of the reactant and the total amount of reactant added to the reaction mixture are within the limits set forth herein before.

In another embodiment of the present invention, the reactant is dissolved in a low-boiling solvent (boiling point below the reaction temperature) and the reactant solution added continuously or in small increments to the reaction vessel containing sulfuric acid maintained at the reaction temperature. As the reactant solution contacts the sulfuric acid, the solvent flashes off and is collected for recycle to another batch, and the reactant reacts to form the product which remains in the sulfuric acid. The rate of addition of the reactant and the total amount of reactant added to the reaction mixture are within the limits set forth herein before.

In the embodiment of the present invention in which a solid acid catalyst is used, the reaction is preferably carried out in a continuous flow fixed-bed reactor system using an inert carrier gas. The 3-chloro-1-(4-chlorophenyl)-1-propanone is fed to the reaction zone as a melt or as a solution in an inert solvent such as 1,2-dichlorobenzene, chlorobenzene, 1,1,2,2-tetrachloroethylene, tetrahydronaphthalene, decahydronaphthalene, nitrobenzene or xylenes. Preferred solvents include 1,2-dichlorobenzene, chlorobenzene, tetrachloroethylene, tetrahydronapthalene, decahydronaphthalene, or xylenes. Most preferred, the starting material is fed as a melt or as a solution in tetrahydronapthalene or 1,2-dichlorobenzene. When a solvent is employed, the concentration of the reactant in the solvent is not limited except by its solubility in the particular solvent selected.

In the embodiment of the present invention in which a solid acid catalyst is used, any practical flow rate of 3-chloro-1-(4-chlorophenyl)-1-propanone per gram of solid acid catalyst may be employed. Preferably, a flow rate of between 0.5–10 g of 3-chloro-1-(4-chlorophenyl)-1-propanone per gram of solid acid catalyst per hour is employed. Lower flow rates are less practical while higher flow rates may result in low conversion to 5-chloro-2,3-dihydro-1H-inden-1-one.

In the embodiment of the present invention in which a solid acid catalyst is used, reaction temperatures between about 200°–425° C. may be beneficially employed. Temperatures between 300°–400° C. are preferred with temperatures between 340°–400° C. being most preferred.

Solid acids can be defined as those materials that have protons or coordinately unsaturated cationic centers on their surface (*Catalysis of Organic Reactions by Supported Inorganic Reagents* by James H. Clark, VCH Publishers, Inc., N.Y., 1994). Based on the above definition, solid acid catalysts are broadly classified into two categories namely, Solid Brønsted Acids and Solid Lewis Acids. The former tends to donate a proton while the latter shows the tendency to accept an electron pair (*New Solid Acids* and *Bases Their Catalytic Properties,* by Tanabe, K., Misono, M., Ono, Y., and Hattori, H., Elsevier, 1989). There are different types of solid Brønsted Acids, viz.

1. Simple oxides (silica, alumina, etc.)
2. Mixed oxides (silica-alumina, zeolites, etc.)
3. Natural and synthetic clay minerals (montmorillonite, etc.)
4. Cation exchange resins (perfluoronated sulfonic acid resins, etc.)
5. Supported acids (sulfuric acid-silica, etc.)
6. Solids containing activated water molecules (hydrated sulfates, etc.)

On the other hand, yttrium triflate, aluminum chloride on silica, etc. are some of the examples of solid Lewis acid catalysts.

In the embodiment of the present invention in which a solid acid catalyst is used, the cyclization reaction may occur on the surface of the catalyst. Reactions that are predominantly surface-catalyzed, may lead to non-selective intermolecular reactions in addition to the desired cyclization reaction. The intermolecular reactions usually give rise to oligomeric byproducts. However, in the case of microporous materials (e.g. zeolites), cyclization reactions are favored over the intermolecular reactions due to the shape and size of the pores and the nature of absorption of the reactant or intermediate moiety inside the pores. The pores of the catalyst should be such that they allow diffusion of the reactant and product moieties yet restrict the formation of larger molecules as a result of intermolecular reactions. In the microporous materials, the intermolecular reactions can be further suppressed by passivating the external surface.

The solid acid catalysts suitable for use in this invention are zeolites. Zeolites are complex aluminosilicates characterized by a three-dimensional framework structure enclosing cavities occupied by ions and water molecules, all of which can move with significant freedom within the zeolite matrix. Most zeolites useful in the process of the present invention can be represented by the following formula:

$$((M)_{2/n}O.Al_2O_3.xSiO_2.yH_2O)$$

wherein M is a cation of valence n; x is 2 or greater; and y is an empirical number determined by the porosity and hydration of the zeolite, generally from 2 to 8. In naturally occurring zeolites, M is principally represented by Na, Ca, K, Mg, and Ba. The cation M is loosely bound to the structure and frequently can be completely or partially replaced with hydrogen or with another cation by conventional ion exchange. When M is completely or predominantly hydrogen, the zeolite is said to be in acid form and designated as H-form.

The zeolite structure consists of cross-linked tetrahedra containing Al or Si atoms in the center and O atoms at the corners. Those tetrahedra are combined in well-defined repeating structures comprising various combinations of 4-, 5-, 6-, 8-, 10-, and 12-membered oxygen-containing rings. The resulting framework consists of regular channels and cages which impart a useful pore structure for catalysis. Pore dimensions are determined by the geometry of the aluminosilicate tetrahedra forming the zeolite channels or cages. For the purpose of this invention, the ring preferably is 10- or 12-membered. In synthetic zeolite Y, the nominal pore size will be about 7.4 Å; in the mordenites, it is about 6.7–7 Å; and in ZSM-5, it is 5.3×5.6 Å and 5.1×5.5 Å. The actual pore size, however, may vary to some extent depending on such factors as the degree of hydration or the presence and location of metal ions. The actual pore size may be determined, if desired, as described in R. M. Barrer, *Hydrothermal Chemistry of Zeolites*, Chapter 1, pp. 20–27, Academic Press, New York, 1982. Further information on zeolites may be obtained from *The Handbook of Molecular Sieves* by R. Szostak, van Nostrand (1992).

The zeolites used in the process of this invention must be in the acid form or H-form. The acid form or H-form, may be obtained, among others, by ammonium exchange followed by calcination, by direct ion exchange with a mineral acid, or by hydrolysis of polyvalent cations. It is believed that acid sites present in these zeolites are responsible for their catalytic activity. For a discussion of acid sites in zeolites, see Dwyer, *Zeolite Structure, Composition, and Catalysis, Chemistry and Industry* (Apr. 2, 1984), pp 258–269. Generally speaking, these acid sites can be either of Brønsted type or of the Lewis acid type, and either type may predominate. However, for the purpose of this invention, it does not appear important which type of acid sites predominate.

Solid acid catalysts suitable for use in the present invention include HZSM-5, HZSM-11, H-Mordenite, H-Y, and H-Beta, which are described in *The Handbook of Molecular Sieves* and have a silicon to aluminum ratios in the range 2.0 to 150. Preferred are HZSM-5 having a silicon to aluminum ratios of 15 to 40 including those that have been surface-treated. The surface treatment of zeolites like those used in Examples 27–29 of Table 1 are described in U.S. Pat. No. 4,752,596 (column 9 line 25 through column 12 line 19). In particular it is useful for the purpose of the invention to surface treat the catalyst to render the external surface of the catalyst inert. This can conveniently be done by treatment of the catalyst with one or more compounds containing at least one element selected from the group consisting of silicon, aluminum, phosphorus and boron, to deposit thereon at least 0.05 weight percent of the element as described in detail in U.S. Pat. No. 4,752,596. All the preferred zeolites will be able to absorb within their pore structure the 3-chloro-1-(4-chlorophenyl)-1-propanone molecule under the conditions described herein above.

The screening of solid acid catalysts for making 5-chloro-2,3-dihydro-1H-inden-1-one were initially performed in 25 mL batch shaker tube reactors. The reactions were conducted at 100° C. to 300° C. with HZSM-5, HY, H-Beta, HZSM-11, H-Mordenite, and HL zeolites, and yttrium triflate as catalysts. In this set of experiments, the reactant polymerized and no EK179 was formed. Based on these results, it was deemed necessary to run the reaction in a continuous flow reactor. In another set of experiments (Examples 7–29), the screening of solid acid catalysts for making 5-chloro-2,3-dihydro-1H-inden-1-one from 3-chloro-1-(4-chloro-phenyl)-1-propanone was performed in a continuous flow stainless steel tube.

In another embodiment of the present invention, the 3-chloro-1-(4-chlorophenyl)-1-propanone starting material can be dehydrohalogenated by treatment with a base and the resulting 3-(4-chlorophenyl)propene-3-one then cyclized to 5-chloro-2,3-dihydro-1H-inden-1-one under the conditions described herein above.

EXAMPLE 1

A 1 L 4-neck round bottom flask was fitted with a mechanical stirrer, thermometer, 500 mL addition funnel and a reflux condenser. The system was placed under a slow purge of nitrogen entering at the top of the addition funnel and exiting from the top of the condenser to a water scrubber. The flask was charged with 100 mL of concentrated sulfuric acid (Baker®, 97%) and 50 mL of sulfuric acid washed n-octane. The mixture was stirred slowly and warmed by means of an oil bath to 105° C. Separately, a mixture of 10.7 g of 3-chloro-1-(4-chlorophenyl)-1-propanone (Aldrich®, 95%) in 200 mL of n-octane was warmed to about 40° C. and filtered warm to remove a small amount of brown insoluble solid. The 3-chloro-1-(4-chlorophenyl)-1-propanone solution was then added dropwise over three hours to the sulfuric acid n-octane mixture. During this time the internal temperature rose to 108° C. and the oil bath temperature rose from 110°–112° C. Heating was continued for 5 minutes after addition was complete and the oil bath then removed. On cooling, the n-octane layer was decanted and the dark red/brown sulfuric acid layer poured, with stirring, over 750 g of crushed ice. The solid which separated was collected by filtration and washed with water (15×50 mL) until the washings were colorless. The remaining dark yellow solid was dried in a vacuum oven at about 40° C. to give 6.69 g of 84% 5-chloro-2,3-dihydro-1H-inden-1-one (by HPLC (25 cm Zorbax® SBC8 eluting with 70:30 water:acetonitrile with UV detection at 294 nm)), m.p. 84°–89° C. The glassware used to handle the product was washed with ethyl acetate, the combined washes dried over magnesium sulfate and the solvent removed under reduced pressure to give an additional 0.27 g of 84% 5-chloro-2,3-dihydro-1H-inden-1-one. The combined yield was 70%.

EXAMPLE 2

The procedure of Example 1 was repeated with the following changes; (a) the oil bath was replaced with an electrical heating mantel; and (b) the initial charge of octane to the reactor was increased to 300 mL. This provided 7.1 g of dark yellow solid which analyzed for 78% 5-chloro-2,3-dihydro-1H-inden-1-one (67% yield).

EXAMPLE 3

The procedure of Example 2 was repeated except that the crude product was washed with about 350 mL of water and then slurried with 500 mL of water and steam distilled. A total of about 1 L of distillate was collected with make up water being added as needed. The first 200 mL of distillate yielded 1.78 g of white solid, m.p. 93°–95° C. The next 400 mL provided an additional 2.74 g of white solid, m. p. 93°–95° C. The final 400 mL gave 0.43 g of white solid, m.p. 92°–94° C. The combined yield was 59% of purified 5-chloro-2,3-dihydro-1H-inden-1-one.

EXAMPLE 4

The procedure of Example 2 was repeated with the reaction being carried out at 115°–116° C. This provided 6.88 g of brown solid which analyzed for 80% 5-chloro-2,3-dihydro-1H-inden-1-one (66% yield).

EXAMPLE 5

The procedure of Example 1 was repeated with the following changes, (a) the oil bath was replaced with an electrical heating mantel and (b) the reaction was carried out at 125° C. This provided 6.6 g of brown solid which analyzed for 87% 5-chloro-2,3-dihydro-1H-inden-1-one (69% yield).

EXAMPLE 6

The procedure of Example I was repeated with the following changes, (a) n-heptane was employed in place of n-octane and (b) the reaction was carried out at 96°–99° C. This provided 6.0 g of brown solid which analyzed for 68% 5-chloro-2,3-dihydro-1H-inden-1-one (53% yield after correction for 0.75 g of 3-chloro-1-(4-chlorophenyl)-1-propanone which was not added due to crystallization in the addition funnel).

EXAMPLES 7–29

The evaluation of solid acid catalysts for making 5-chloro-2,3-dihydro-1H-inden-1-one from 3-chloro-1-(4-chlorophenyl)-1-propanone was performed in a continuous flow stainless steel tube (13 mm O.D., 11 mm I.D., and 40 cm long) with appropriate Swagelock® fittings to connect the feed delivery unit, product recovery unit and a thermocouple. Heating of the reactor was achieved by enclosing it in a tube furnace with refractory embedded heating elements which maintained uniform temperature across the reaction zone. The reactor temperature was metered and monitored by thermocouples embedded in the midpoint of the catalyst bed and the external wall of the microreactor.

The reactor feed system was designed to allow vapor and liquid feeds into the reaction zone at a constant flow rate. The gases were metered and monitored using Brooks® mass flow controllers and the liquid reagents were pumped to the reactor using an Isco syringe pump.

The product stream or effluent from the reactor was directed to a trapping system comprised of an ice-cooled trap followed by two consecutive dry ice traps. The volatile organics were condensed and collected for work up and analysis. Any uncondensed vapors were directed to two scrubbers, set in series. The inert unscrubbed gases were vented to the atmosphere. Product identification and quantitation was achieved using one or more of the following techniques; gas-chromatography, mass spectrometry and nuclear magnetic resonance.

In an experiment of Examples 7–29, the catalyst was calcined in air by heating to 550° C. at a rate of 60° C./hr and holding at 550° C. for 6 hr. It was then allowed to cool down to 120° C. and 3–5 gm of the same catalyst was packed in the reactor. The catalyst bed was preceded and followed by layers of inert packing materials, such as quartz or silicon chips to provide better heat transfer to the incoming feed stream. A blank run (13) was performed with the reactor filled with quartz chips. The results are shown in Table 1.

| Example Numbers | Catalyst | Si/Al Ratio | Solvent[1] | Amt of Cat. (gm) | Amt of DCP[2] (wt %) | Flow rate (gm/hr) | Temp. (°C.) | TOS[3] (hr) | Yield (%) |
|---|---|---|---|---|---|---|---|---|---|
| 7  | HZSM-5            | 25   | TCE  | 2.001 | 11.8  | 8.9  | 350 | 4.0  | 55.9 |
| 8  | HZSM-5            | 25   | TCE  | 2.000 | 11.8  | 8.9  | 340 | 7.3  | 50.4 |
| 9  | HY                | 97   | TCE  | 2.001 | 11.8  | 8.9  | 350 | 4.0  | 3.8  |
| 10 | HZSM-5            | 25   | TET  | 3.000 | 21.0  | 5.7  | 360 | 6.0  | 60.4 |
| 11 | HZSM-5            | 25   | NB   | 3.000 | 11.8  | 8.9  | 340 | 6.1  | 8.9  |
| 12 | HZSM-5            | 25   | XYL  | 3.001 | 21.0  | 5.2  | 350 | 6.0  | 45.6 |
| 13 | BLANK             | —    | ODCB | 0.000 | 12.0  | 6.1  | 350 | 8.0  | 0.0  |
| 14 | H-Beta            | 12.5 | ODCB | 3.000 | 21.0  | 5.7  | 350 | 8.5  | 16.9 |
| 15 | HZSM-5            | 25   | ODCB | 3.000 | 21.0  | 7.0  | 300 | 8.0  | 60.6 |
| 16 | HZSM-5            | 25   | ODCB | 3.001 | 21.0  | 6.9  | 340 | 6.0  | 64.9 |
| 17 | HZSM-5            | 25   | ODCB | 3.001 | 21.0  | 6.7  | 350 | 7.8  | 64.9 |
| 18 | HZSM-5            | 25   | ODCB | 3.001 | 21.0  | 7.2  | 350 | 12.0 | 63.4 |
| 19 | HZSM-5            | 25   | ODCB | 3.001 | 21.0  | 6.9  | 375 | 8.0  | 59.2 |
| 20 | HZSM-5 Extrd.[4]  | 25   | ODCB | 4.000 | 21.0  | 7.1  | 350 | 7.5  | 54.4 |
| 21 | HZSM-5 Extrd.     | 25   | ODCB | 4.000 | 21.0  | 7.0  | 350 | 10.0 | 54.2 |
| 22 | HZSM-5 Extrd.     | 25   | ODCB | 4.000 | 21.0  | 7.0  | 350 | 12.0 | 49.4 |
| 23 | HZSM-5            | 15   | None | 5.000 | 100.0 | 1.23 | 360 | 12.0 | 59.6 |
| 24 | HZSM-5            | 25   | None | 5.000 | 100.0 | 1.22 | 360 | 12.0 | 70.8 |
| 25 | HZSM-5            | 40   | None | 5.000 | 100.0 | 1.17 | 360 | 12.0 | 70.1 |
| 26 | HZSM-5            | 50   | None | 5.000 | 100.0 | 1.29 | 360 | 8.0  | 71.1 |
| 27 | HZSM-5 TEOS[5]    | 25   | ODCB | 4.000 | 100.0 | 6.3  | 360 | 8.0  | 60.7 |
| 28 | HZSM-5 TEOS       | 25   | None | 5.000 | 100.0 | 1.34 | 360 | 8.0  | 84.7 |
| 29 | HZSM-5 Extrd./TEOS| 25   | None | 5.000 | 100.0 | 1.25 | 360 | 12.0 | 62.5 |

[1]TCE = 1,1,2,2-tetrachloroethylene, TET = tetrahydronaphthalene, NB = nitrobenzene, XYL = xylenes, ODCB = 1,2-dichlorobenzene.
[2]DCP = 3-chloro-1-(4-chlorophenyl)-1-propanone.
[3]TOS = Time on Stream.
[4]Extrd. = Extrudate.
[5]TEOS = Tetraethylorthosilica-treated HZSM-5.

We claim:
1. A process for making 5-chloro-2,3-dihydro-1H-inden-1-one comprising contacting 3-chloro-1-(4-chlorophenyl)-1-propanone with a catalyst selected from sulfuric acid and solid acid catalysts having a silicon to aluminum ratio of 2.0 to 150, the sulfuric acid catalyst being used at a temperature of 90°–150° C. under conditions wherein a solution of the reactant in an inert solvent is added to the reaction mixture, which mixture comprises any 5 chloro-2,3-dihydro-1H-inden-1-one already produced, sulfuric acid, and any 3-chloro-1-(4-chlorophenyl)-1-propanone not yet reacted, at a rate of 0.05–1.0 moles of 3-chloro-1-(4-chlorophenyl)-1-propanone per liter of sulfuric acid per hour, and the solid acid catalyst being used at a temperature of 200°–425° C. under conditions where the 3-chloro-1-(4-chlorophenyl)-1-propanone is fed to the catalyst at a flow rate of 0.5–10 grams of 3-chloro-1-(4-chlorophenyl)-1-propanone per gram of catalyst per hour.

2. The process of claim 1 wherein the catalyst is sulfuric acid, and the temperature is maintained at 100°–125° C.

3. The process of claim 1 wherein the catalyst is sulfuric acid and the concentration of the 3-chloro-1-(4-chlorophenyl)-1-propanone in the solvent 0.1 to 1.0 molar.

4. The process of claim 1 wherein the catalyst is a solid acid catalyst, and the temperature is maintained at 340°–400° C.

5. The process of claim 1 wherein the catalyst is HZSM-5 with a silicon to aluminum ratio of 15 to 40.

6. The process of claim 5, wherein the catalyst is surface treated to render the external surfaces of the catalyst inert.

7. The process of claim 6, wherein the catalyst is surface treated with tetraethylorthosilicate.

8. The process of claim 1 wherein the catalyst is a solid acid catalyst, and the reactant 3-chloro-1-(4-chlorophenyl)-1-propanone is fed to the catalyst as a solution in an inert solvent at a concentration of 10–100 weight percent in the solvent.

9. The process of claim 8 wherein the solvent is selected from chlorobenzene and 1,2-dichlorobenzene.

10. The process of claim 1 wherein the catalyst is a solid acid catalyst and the reactant 3-chloro-1-(4-chlorophenyl)-1-propanone is fed to the catalyst as a melt.

* * * * *